United States Patent [19]

Cals et al.

[11] 4,343,312

[45] Aug. 10, 1982

[54] PACEMAKER OUTPUT CIRCUIT

[75] Inventors: Guillaume L. M. Cals, Dieren; Frederik H. M. Wittkampf; Kornelis A. Mensink, both of Brummen; Hendrik L. Brouwer, Dieren, all of Netherlands

[73] Assignee: Vitafin N.V., Curacao, Netherlands Antilles

[21] Appl. No.: 231,889

[22] Filed: Feb. 5, 1981

Related U.S. Application Data

[63] Continuation-in-part of Ser. No. 30,457, Apr. 16, 1979, Pat. No. 4,305,396.

[51] Int. Cl.³ .............................................. A61N 1/36
[52] U.S. Cl. ................................................ 128/419 PG
[58] Field of Search ................... 128/419 PG, 419 PT

[56] References Cited

U.S. PATENT DOCUMENTS

| 3,563,247 | 2/1971 | Bowers | 128/422 |
| 3,683,934 | 8/1972 | Bukowiecki et al. | 128/419 PG |
| 3,835,865 | 9/1974 | Bowers | 128/419 P |
| 3,845,773 | 11/1974 | Fontaine et al. | 128/419 PG |
| 3,881,493 | 5/1975 | Cannon | 128/419 PG |
| 3,924,641 | 12/1975 | Weiss | 128/419 PG |
| 4,055,189 | 10/1977 | Auerbach et al. | 128/419 PG |
| 4,114,627 | 9/1978 | Lewyn et al. | 128/419 PT |
| 4,170,999 | 10/1979 | Allen et al. | 128/419 PG |

FOREIGN PATENT DOCUMENTS 2520730  11/1975  Fed. Rep. of Germany ...... 128/419 PG Primary Examiner—William E. Kamm
Attorney, Agent, or Firm—Woodcock, Washburn, Kurtz, Mackiewicz & Norris

[57] ABSTRACT

A physiological stimulating system includes improved means for minimizing the polarization that results at the stimulus site, thereby enabling enhanced detection of evoked responses. In the pacemaker embodiment, the stimulus signal comprises positive recharge pulses immediately before and immediately after the negative stimulus signal, the recharge pulses being adapted in a time duration and amplitude such that the total current delivered to the stimulus site, (e.g., a patient's heart) by the stimulus signal is substantially zero.

6 Claims, 7 Drawing Figures

PACEMAKER OUTPUT CIRCUIT

This application is a continuation-in-part of U.S. application Ser. No. 30,457, filed Apr. 16, 1979, now U.S. Pat. No. 4,305,396 titled "Improved Rate Adaptive Pacemaker". All of the disclosure of that application is incorporated herein by reference.

This application Ser. No. 231,882 is related to the application filed concurrently herewith and titled APPARATUS FOR PHYSIOLOGICAL STIMULATION AND DETECTION OF EVOKED RESPONSE, invention of Frederik H. M. Wittkampf, Kornelis A. Mensink and Hendrik L. Brouwer.

BACKGROUND OF THE INVENTION

This invention lies in the field of physiological stimulus systems, e.g. pacemaker systems, and in particular implantable systems for physiological stimulation and detection of the response evoked by stimulation.

For the operation of conventional demand type pacemakers, it is necessary to sense the natural QRS signals which are developed in the ventricle, so as to cause resetting of the pacemaker oscillator. The state of the art permits reliable sensing of the natural QRS signal, as is seen from the widespread use of demand pacers. It is noted that, in demand pacer operation, the QRS signal occurs at least a full heartbeat period following the last stimulus pulse, if any, such that conditions in the vicinity of the electrode are relatively quiescent. By contrast, immediately after delivery of a negative going stimulus pulse, there is a large polarization signal present at the electrode, due to the condition of the adjacent heart tissue cells and the effective capacitance of the electrode itself. Since it takes some time for this polarization signal to dissipate it has the effect of masking signals which occur shortly thereafter, e.g., the evoked QRS or evoked T wave signals.

The area of threshold tracking pacemakers best illustrates the problem generated due to the polarization signal at the electrode following delivery of a stimulus pulse. A threshold tracking system is illustrated in U.S. Pat. No. 3,920,024, incorporated herein by reference. To date, there has been no significant commercial use of the implantable threshold tracking pacer, primarily due to the difficulty of detecting the resulting evoked signal in the midst of the polarization signal. Threshold tracking pacers are discussed at length in the literature, and there has been a limited use of external threshold tracking pacers, for various clinical applications. However, they have not achieved the prominence that was predicted some years back, due to the essentially unsolved problem of reliably and accurately picking the evoked QRS signal out of the overall signal which is present at the electrode shortly after delivery of the stimulus. It is clear that the inability to accurately and reliably sense the presence or absence of an evoked heartbeat is critical to the performance of a threshold tracking pacemaker.

The advantage of the threshold tracking pacemaker has been questioned recently, due to the greatly increased power capacity of the lithium battery as compared to prior mercury zinc batteries. The threshold tracking pacemaker would save a considerable amount of energy, and thereby extend pacer lifetime substantially, due to the fact that stimulus pulses would be delivered at or near threshold, instead of at a level which provided a safety factor of 2 or 3 times. Since present day lithium batteries extend the pacer lifetime to 12 to 15 years, this foreseen relative advantage of the threshold tracking pacemaker is greatly attenuated. However, other developments which are foreseeable continue to make it desirable to achieve a solution which would permit a reliable threshold tracking pacemaker. The ability to monitor threshold and to process information obtained from the evoked heartbeat may be quite useful in future pacemaker models, such as for providing a diagnostic aid in determining patient condition. As set forth in the referenced patent application, monitored patient threshold may be used to control the rate of delivery of stimulus signals. Also, changes in electrode construction and improvements in programability are expected to enhance the value of threshold tracking and, more generally, the value of being able to continuously monitor both evoked and natural heartbeat signals.

While the utility of the subject invention is best described in the pacemaker, or pacing system embodiment, it is to be understood that the invention has utility in other systems for physiological stimulation. The invention may be practiced in any application where it is desired to quickly determine the physiological response to an applied stimulus by detection of the resulting evoked electrical characteristic at the location of applied stimulus.

SUMMARY OF THE INVENTION

It is an object of this invention to provide a pacing system for delivering stimulus signals to a patient's heart, wherein the sensed polarization immediately following delivery of a stimulus signal is minimized.

It is another object of this invention to provide a pacing system which enables quicker and more accurate sensing of an evoked response following delivery of a stimulus.

It is another object of this invention to provide an improved pacing system and method for threshold tracking.

It is another object of this invention to provide an improved pacemaker system for sensing heartbeat signals substantially immediately following delivery of stimulus signals, the system providing for delivery of recharge pulses of optimum level and timing so as to balance out the polarization effect of a delivered stimulus signal.

In accordance with the above, there is provided an improved system for delivery of physiological stimulus signals, such as a cardiac pacemaker, which system is characterized by having output means for providing a stimulus signal, each of said signals being constituted of a series of alternating polarity pulses of respective time durations and signal levels so as to minimize the resulting polarization at the point of delivery of such signals. In particular, the stimulus signal of this invention comprises a first recharge pulse of positive polarity, followed by a negative stimulus pulse and then a succeeding positive recharge pulse, the series of pulses having a time duration which is very small compared to the time period between delivered stimulus signals.

DESCRIPTION OF THE PREFERRED EMBODIMENT

Figure 1:
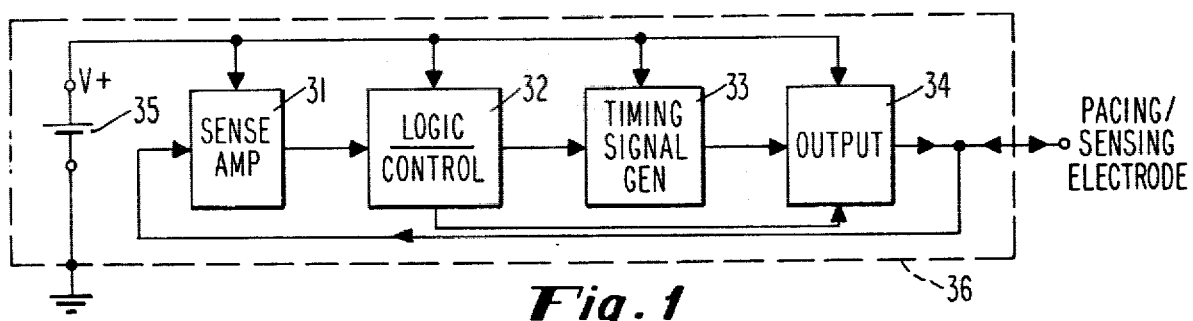
FIG. 1 is a block diagram showing the primary components of a pacing system utilizing this invention.

Referring now to FIG. 1, there is shown a block diagram illustrating the essential components of the pacing system utilizing this invention. The invention is illustrated in terms of a demand pacer, the features of which are well known in the art. A sense amplifier 31 detects the presence of a QRS signal, and connects a signal to a logic/control circuit 32 when a QRS has been sensed. In a threshold tracking embodiment, such as illustrated in U.S. Pat. No. 3,920,024, amplifier 31 must detect the evoked response which follows the stimulus in about 10 to 50 ms. The circuitry of block 32 performs the normal logic functions of a demand pacer such as distinguishing a sensed natural QRS signal, timing out a refractory interval, etc. For programmable pacemakers, stored information relative to pacing parameters and other program control features may be considered to be found in block 32. Also, block 32 suitably contains the desired circuitry for employing the evoked response information, e.g., tracking threshold. As illustrated, control signals may be transferred from block 32 to output 34, for controlling the output in accordance with programmed signals or for threshold tracking. Block 33 is the basic timing generator, which establishes the rate at which the pacer delivers stimulus pulses in the absence of natural patient pulses. As is known in the art, if the timing generator times out on its own, meaning that a stimulus is to be delivered, the timing signal is connected to an output circuit 34. If a signal comes from circuit 32 prior to time out in circuit 33, which signal indicates that a natural QRS has been detected, the timing generator 33 is reset without triggering an output. Output 34 represents circuitry which is utilized in generating a desired output signal, commonly referred to as an output pulse, of desired value in terms of pulse width, voltage or current. As shown further in FIG. 1, the output 34 is connected to a pacing/sensing electrode which is the end of a pacing lead (not shown), which lead provides the necessary electrical connection between the pacemaker and the patient's heart. An electrical path is illustrated between the output of circuit 34 and the input of sense amplifier 31. Further, power is provided, suitably by a lithium type battery or any other desired source, as illustrated at 35. For unipolar pacing systems, the terminal of source 35 shown as ground is generally connected to the case of the pacemaker, illustrated at 36.

Figure 2A:
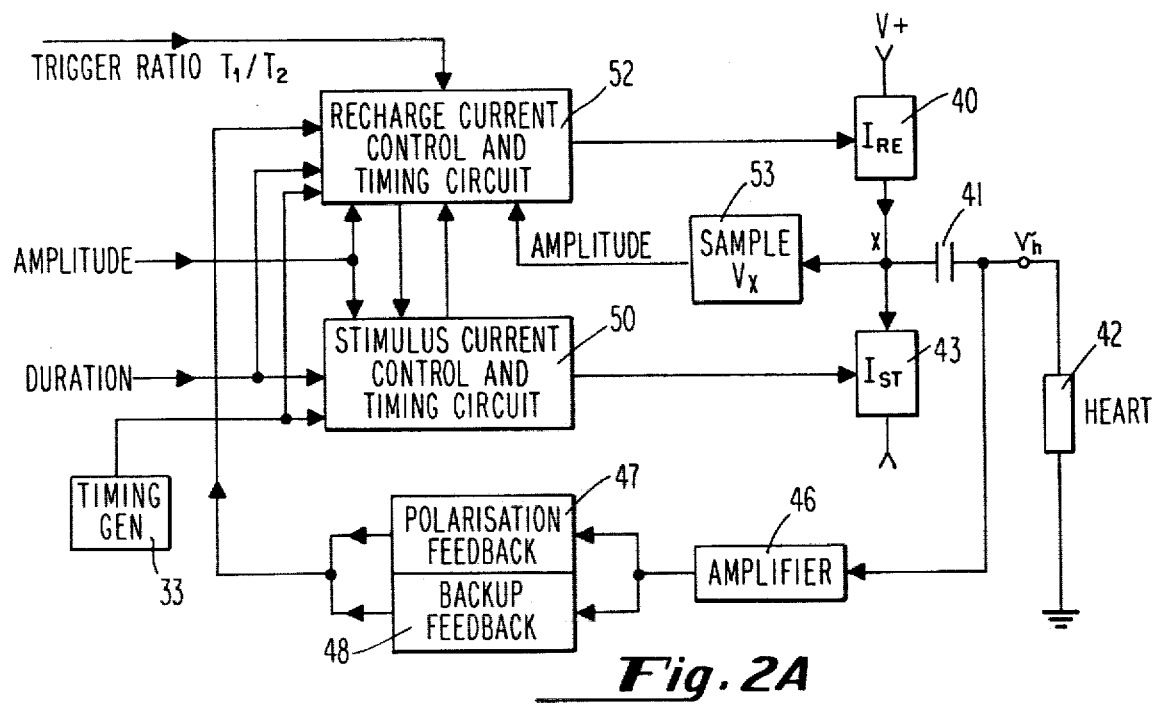
FIG. 2A is a block diagram showing a current control embodiment of the output stage of the system of this invention.

Referring now to FIG. 2A, there is shown a block diagram of an embodiment of output circuit 34 which is based upon current control of the component pulses of the delivered stimulus signal. As used in this application, the term "stimulus signal" shall refer to the group or series of pulses delivered, the negative going pulse of which is the component which actually provides the stimulus. Also, the term pulse is used in a general manner, it being understood that a pulse as actually generated and used within this invention is not confined to a sharp signal in the time domain, but may be a sloped, exponential or other form of nonlinear signal.

In FIG. 2A, the primary circuit components which generate the stimulus signal are the two current generators, namely the recharge current generator 40 and the stimulus generator 43. These two current generators are shown as ideal circuits and can be constructed in any conventional manner. They are suitably switchable on-off circuits, such that they can be turned on and off sharply, such as can be accomplished by putting a control voltage on the gate of a FET transistor or the like. When recharge current generator 40 is on, and stimulus current generator 43 is off, a current flows from V+ through the generator, through the capacitor 41 which charges up, and through the heart 42 to ground, thereby applying a positive polarity signal to the heart. When stimulus current generator 43 is on, and recharge generator 40 is off, current flows up through heart 42 as seen in the drawing, through capacitor 41 (thereby discharging it) and down through current generator 43, delivering a negative pulse to the heart. The size of the negative going pulse is designed, in accordance with well known principles, to evoke stimulation of the heart.

Figure 2B:
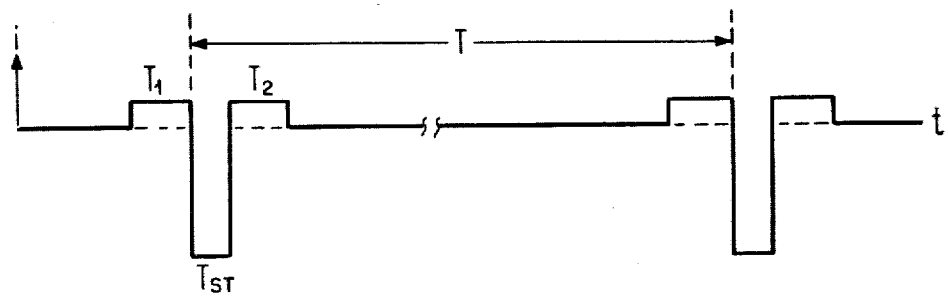
FIG. 2B is a curve depicting the timing of stimulus signals delivered by the system of this invention.
Figure 2C:
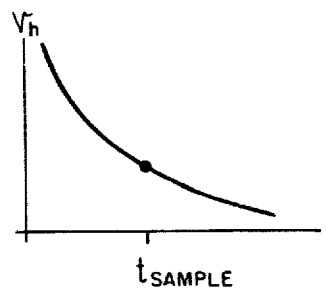
FIG. 2C is a curve illustrating the sampling of the polarization at the heart for use in the polarization feedback branch of the circuit of FIG. 2A.

As seen in FIG. 2B, recharge generator 40 is first triggered for a time $T_1$ to produce a first positive delivery of current to the heart, stimulus generator 43 is then turned on for a time $T_{st}$ to deliver the negative stimulating component, and then recharge generator 40 is turned on again for a time $T_2$ to deliver another discharge pulse. These three pulses, preferably time contiguous as shown, constitute the total stimulus signal which is delivered periodically by the pacemaker when no natural heart signal is detected.

In practice, the respective times $T_1$ and $T_2$ and the current levels of the recharge pulses are controlled by recharge current control and timing circuit 52. As shown, this circuit receives program information, suitably from block 32, for determining the ratio $T_1/T_2$, the amplitude of the recharge pulses, and the duration of each. In a similar manner, stimulus current control and timing circuit 50 controls the stimulus component delivered by current generator 43, and receives amplitude and duration program signals. Both circuits 52 and 50 receive basic timing signals from the timing generator 33, to determine when the series of pulses, or the overall stimulus signal is to be generated. As shown by the arrows between blocks 52 and 50, the timing signal may be connected from block 52 at the end of the first recharge pulse to trigger a stimulus pulse, and another timing signal may be connected from block 50 and 52 at the end of the stimulus pulse to trigger the second recharge signal. It is understood that timing circuitry is well known in the art, and the time durations $T_1$ and $T_2$ may be provided conveniently by one-shot or monostable multi-vibrators or their equivalent, or other digital timing mechanisms well known in the art.

The embodiment of FIG. 2A provides two or three feedback loops. Block 53 is shown connected to point X, between the two current generators, which block measures the voltage at such point X at a predetermined time between stimulus signals. By determining the variation, if any, of $V_X$, the circuit can measure whether the net charge delivered through capacitor 41 during the preceeding impulse group is zero. If, due to improper balancing between positive and negative output currents, or for any other reason of instability, $V_X$ has changed, an amplitude feedback signal is applied to block 52 to change the value of the recharge current. As long as the total charge delivered by the two recharge pulses and the stimulus charge is substantially zero, the voltage at point X, as sampled between stimulus signals, will not vary significantly.

A second feedback branch is connected between the output at the heart and the recharge control circuit 52. The heart voltage $V_h$ is sampled at a sample time shortly after termination of $T_2$, to determine the polarization level. The polarization level is compared to a reference at block 47, and an output signal connected to block 52 to change the ratio $T_1/T_2$ of the recharge pulses for succeeding stimuli. For further improvement the reference value can be related also to the stimulus duration ($T_{st}$) and/or amplitude. Changing the ratio of $T_1$ to $T_2$ changes the polarization decay characteristic, and by this means the residual polarization can be optimally reduced. A second branch 48 of this feedback loop samples $V_h$ following the delivery of a backup pulse for a threshold tracking system. It is to be understood that for a threshold tracking system where a series of backup pulses is delivered until response is evoked, $V_h$ may be monitored following each of such backup pulses.

For the circuit of FIG. 2A, the duration $T_1$ of the first recharge pulse is determined by the stimulus duration input, as well as the $T_1/T_2$ ratio information. The amplitude is determined by the program amplitude of the stimulus current, as well as the feedback through block 53. The stimulus pulse duration $T_{st}$ is determined by the stimulus duration information, while the stimulus amplitude is determined by the stimulus amplitude input. The second recharge pulse duration $T_2$ is determined by the $T_1/T_2$ ratio and by the stimulus duration input, while the amplitude is determined by the stimulus current input and by the feedback through block 53. It is important that the total charge of the two recharge pulses be substantially equal to the charge of the stimulus portion, such that the net charge delivered to the heart by the stimulus signal is substantially zero. It need not be precisely zero, since further recharge can be accomplished following recharge pulse $T_2$ and before the next stimulus signal. However, in order to minimize the polarization at the sensing electrode following the termination of the second recharge pulse, the net charge delivered by the three pulse components should be substantially zero. In practice, $T_1$ plus $T_2$ may be approximately 4 times $T_{st}$, although this ratio may go up to 10 or more. It is, however, important that the second recharge pulse not be too long, since the evoked response can hardly be sensed until the second recharge pulse is terminated. Conversely, there is a limit in the amplitude of the two recharge pulses, since it has been found that if these pulses are made too high in amplitude this causes some reduction in the stimulation efficiency.

The advantage of the circuit of FIG. 2A is that the polarization is compensated for very accurately. This is an active system which measures the polarization, and forces adjustments through the feedback loops so as to reduce the polarization to a minimum. The disadvantages are the use of two or more feedback systems, and the extra current consumption due to the complexity of the circuit.

Figure 3A:
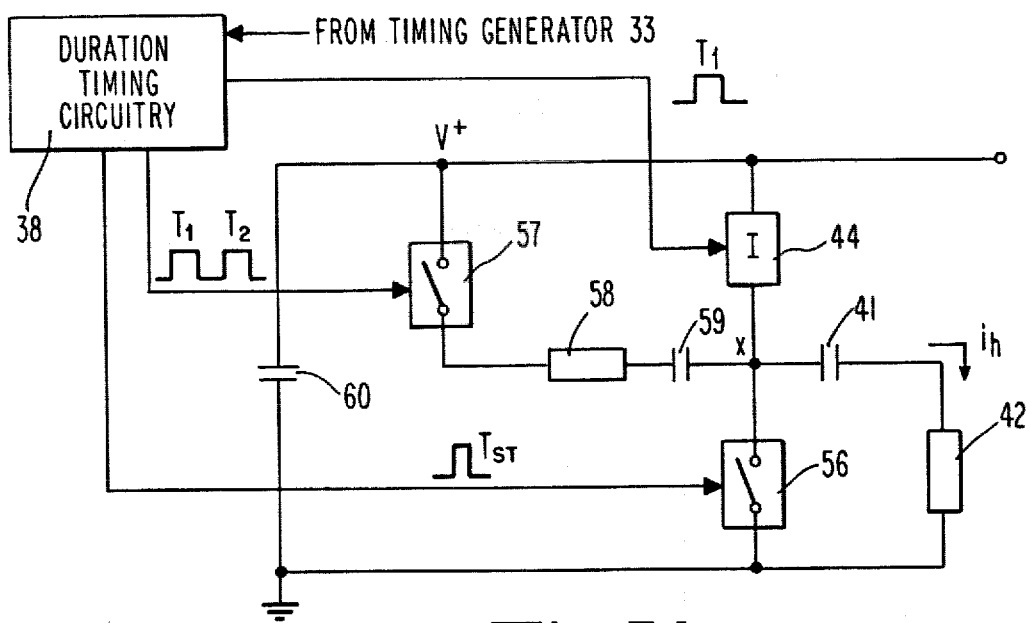
FIG. 3A is a circuit diagram showing a preferred form of generating a three pulse stimulus signal in accordance with the system and method of this invention.
Figure 3B:
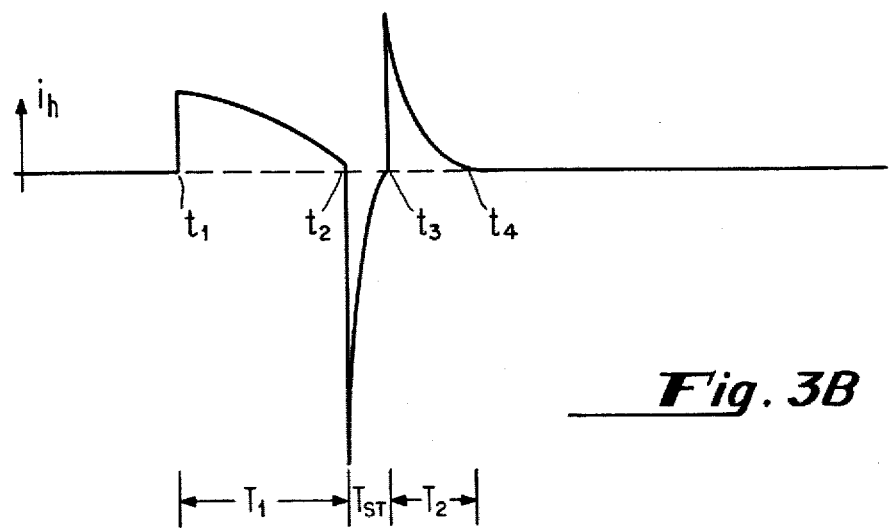
FIG. 3B is a timing diagram illustrating the current delivered to the heart by a stimulus provided by the circuit of FIG. 3A.
Figure 3C:
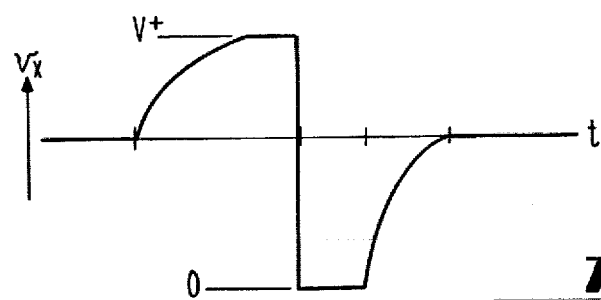
FIG. 3C is a timing diagram showing the voltage at point X of the circuit of FIG. 3A.

Referring now to FIGS. 3A, 3B and 3C, there is illustrated a preferred embodiment of the output circuit for the practice of this invention. This circuit is preferred because of its relative simplicity. In this embodiment a signal charging block 44 is illustrated for charging output capacitor 41. Block 44 may be a current generator, or may be any conventional circuit for providing a voltage pulse suitable for charging capacitor 41. When circuit 44 is on it provides current which is connected through capacitor 41 and the heart 42, providing a positive impulse to the heart. Also connected to capacitor 41 at point X is a switch 56, suitably a semi-conductor switch which may be controlled in an off-on state in a conventional manner. Another loop from point X back to V+ is provided by capacitor 59 in series with resistor 58 and switch 57. A power supply decoupling capacitor 60 is illustrated between V+ and ground. Duration timing circuitry block 38 is shown for generating timing signals corresponding to durations $T_1$, $T_2$ and $T_{st}$. As stated before, these timing signals may be generated in any convenient well known manner, either from a clock source in a digital pacer or by analog timing circuits such as a one-shot generator.

In practice, during time $T_1$, circuit 44 is enabled, causing charging of capacitor 41 and causing a positive recharge pulse to be delivered to the heart. At the same time, during duration $T_1$, switch 57 is closed. Assuming that the voltage at point X had been at some value between O and V+ time $t_1$, capacitor 59 discharges such that both sides of it are at substantially V+. At time $t_2$, note that the voltage at point X has reached V+ as seen in FIG. 3C. At time $t_2$ switch 56 is closed, switch 57 is open and circuit 44 is off. During duration $T_{st}$ the charge on capacitor 41 discharges through the heart, providing the negative stimulation pulse, while there is no change in the charge on capacitor 59. At time $t_3$, switch 56 opened again and switch 57 closes for time $T_2$. During time $T_2$, or until $t_4$, there is a path from V+ to ground through switch 57, resistor 58, and capacitors 59 and 41. Capacitor 41 recharges to some value intermediate ground and V+, dependent upon the relative value of capacitors 59 and 41. This provides the second positive recharge pulse. At time $t_4$, switch 57 is opened again, and the circuit remains quiescent until the next signal from timing generator 33.

In practice, for the circuit of FIG. 3A, the duration $T_1$ may be typically about 6–10 ms, although this is not a critical value. The amplitude of $T_1$ may be suitably 1 ma. The stimulus pulse duration $T_{st}$ is typically 0.1–1 ms, and the amplitude is dependent on the heart impedence. The duration of the second recharge pulse $T_2$ may be 3.5–10 ms, the amplitude again being dependent on heart impedence. Note that when the circuit is stabilized the total net charge delivered by the series of three pulses is 0, or otherwise the voltage $V_x$ would continually change. It is found in practice that it takes a few pulses for the circuit to stabilize such that $V_x$ remains substantially constant from stimulus to stimulus. Note that in threshold tracking, where it is desired to change the stimulus supply level in steps, this affects the stabilization of the circuit. For such case the stabilization may be improved by rearranging the circuit to connect the heart to V+ instead of ground. However, it is more convenient to change stimulus duration.

Although the emphasis of the system and method of this invention is in the generation of the plural pulse stimulus signals, it is to be understood that additional improvement may be made through optimum design of the sense amplifier. The sense circuit may suitably comprise a sample and hold circuit, used to compensate for any detected polarization signal level. Likewise, current amplifier circuitry for providing current amplification of the input signal may be utilized to aid in discharge of the polarization signal at the system electrode.

In summary, it is noted that in order to effectively practice the system and method of this invention the stimulus signal must contain recharge components optimized to balance out the polarization affect of the negative going stimulus signal. While some improvement may be obtained simply by providing a sharp recharge pulse following the stimulus level, applicants have determined that substantial improvement is obtained when the negative stimulus pulse is immediately preceded by a positive recharge pulse. The system may be fine tuned by adjusting the relative timing of the preceding and following recharge pulses. It is emphasized that the invention does not reside in the precise switching circuitry utilized for generating the components of the stimulus signal, as these can be generated with conventional analog or digital circuits. Applicant has not determined that there exists any preferred circuitry as such for carrying out the switching. However, the embodiment illustrated in FIG. 3A is considered a preferred embodiment for a pacemaker system due to its simplicity, relatively low current drain and thus suitability for incorporation into an implantable pacemaker. While it has been determined that the 3 pulse arrangement provides excellent improvement in reducing the detected polarization following stimulus, improvement is accomplished by utilizing a positive recharge pulse prior to the negative stimulus pulse, even without a second recharge pulse. Such a recharge pulse is suitably no more than 10 ms, since a natural QRS can hardly be sensed during the recharge pulse. If a second recharge pulse is utilized, it is preferably of short time duration, so that the evoked response can be sensed as quickly as possible.

We claim:

1. A pacemaker of the type for delivering pacing stimulus signals to a patient's heart, having an output circuit for generating said pacing stimulus signals, a timing generator for timing the generation of said pacing stimulus signals, sensing means for sensing heartbeat signals from said patient's heart, and logic means connected to said sensing means and said timing generator for controlling generation of said pacing stimulus signals, wherein said output circuit is characterized by a coupling circuit having an output capacitor, for coupling said stimulus signals to said patient's heart;

a charging circuit connected to said coupling circuit and having switchable circuit means for providing a first charging current to charge said output capacitor during a first predetermined time duration;

a first switching circuit connected to said coupling circuit and having means for providing discharge of said output capacitor for a second time duration, thereby providing a negative stimulus pulse to said heart; and a second switching circuit with a capacitance element, connected to said coupling circuit, and having means for providing a second charging current to said output capacitor circuit during a third time duration.

2. The pacemaker as described in claim 1, wherein said charging circuit comprises first timing means for switching said switchable circuit means to provide said charging current for said first time duration;

said first switching circuit comprises second timing means for switching said first switching circuit so as to provide a path for discharging said output capacitor for said second time duration; and said second switching circuit comprises third timing means for switching said second switching circuit to provide said second charging current for said third time duration.

3. The pacemaker as described in claim 1, wherein said three time durations are contiguous in time.

4. The pacemaker as described in claim 1, wherein the total net charge delivered by said output circuit during said three time durations is substantially zero.

5. The pacemaker as described in claim 1, wherein said output circuit normally delivers said pacing signals periodically, and each of said pacing signals comprises in succession said first charging current, said negative stimulus pulse, and said second charging current.

6. The pacemaker as described in claim 1, wherein said second switching circuit has means for charging said capacitance element during said first predetermined time duration.

* * * * *